United States Patent
Wagner

(10) Patent No.: US 10,101,327 B2
(45) Date of Patent: Oct. 16, 2018

(54) ENHANCING SEROLOGICAL ASSAYS VIA FUSION PROTEINS

(71) Applicant: Cornell University, Ithaca, NY (US)

(72) Inventor: Bettina Wagner, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/261,212

(22) Filed: Sep. 9, 2016

(65) Prior Publication Data

US 2017/0067896 A1    Mar. 9, 2017

Related U.S. Application Data

(60) Provisional application No. 62/216,010, filed on Sep. 9, 2015.

(51) Int. Cl.
*G01N 33/569* (2006.01)
*G01N 33/543* (2006.01)

(52) U.S. Cl.
CPC ..... *G01N 33/569* (2013.01); *G01N 33/54306* (2013.01); *G01N 2469/20* (2013.01)

(58) Field of Classification Search
None
See application file for complete search history.

(56) References Cited

U.S. PATENT DOCUMENTS

2011/0287454 A1* 11/2011 Wagner ............... C07K 16/00
435/7.92

OTHER PUBLICATIONS

Wagner and Freer (Veterinary Immunology and Immunopathology. 2009; 127: 242-248).*
Keggan et al. (Veterinary Immunology and Immunopathology. 2013; 153: 187-193).*
Soboll et al. (Veterinary Immunology and Immunopathology. 2006; 111: 81-95).*
Haijan-Tilaki, K. "Receiver Ooperating Characteristic (ROC) Curve Analysis for Medical Diagnostic Test Evaluation", Caspian J. Intern. Med., (2013), 4(2): 627-635.
Kydd, J.H. et al., "The equine immune response to equine herpesvirus-1: The virus and its vaccines", Veterinary Immunology and Immunopathology, (2006), 111, 15-30.
Wagner, B. et al., "Horse cytokine/IgG fusion proteins—mammalian expression of biologically active cytokines and a system to verify antibody specificity to equine cytokines", Veterinary Immunology and Immunopathology, (2005), 105, 1-14.
Wagner, B. et al., "Monoclonal antibodies to equine CD23 identify the low-affinity receptor for IgE on subpopulations of IgM+ and IgG1+ B-cells in horses", Veterinary Immunology and Immunopathology, (2012), 146, 125-134.
Wagner, B. et al., "Antibody and cellular immune responses of naive mares to repeated vaccination with an inactivated equine herpesvirus vaccine", Vaccine, (2015), 33, 5588-5597.

* cited by examiner

*Primary Examiner* — Shanon A. Foley
(74) *Attorney, Agent, or Firm* — Scully Scott Murphy & Presser

(57) ABSTRACT

A serological assay with an improved linear range of detection is disclosed using a fusion protein system, such as an anti-cytokine/cytokine fusion protein (ACYF) system, for evaluating immune responses. Also disclosed are related compositions, fusion proteins, expression vectors, monoclonal antibodies, and kits for practicing the assay method of the present invention.

24 Claims, 6 Drawing Sheets
Specification includes a Sequence Listing.

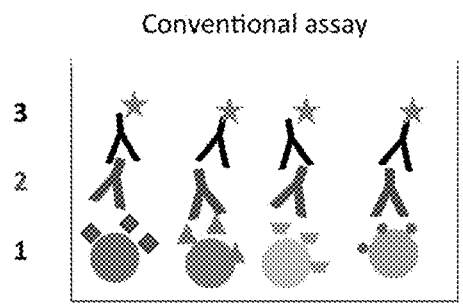
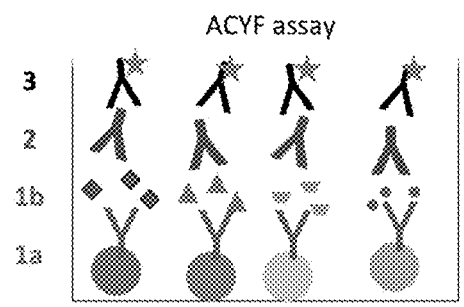
1 = bead conjugated with different antigens
2 = patient sample
3 = anti-Ig antibody conjugated to fluorochrome or enzyme
1a = bead conjugated with anti-cytokine mAb
1b = different cytokine/antigen fusion proteins
2 = patient sample
3 = anti-Ig antibody conjugated to fluorochrome or enzyme
Figure 1A
Figure 1B

Figure 2A

Figure 2B

SEQUENCE LISTING

```
<160> NUMBER OF SEQ ID NOS: 3

<210> SEQ ID NO 1
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 1
gcggccgcat gggtctcacc taccaactg                                  29

<210> SEQ ID NO 2
<211> LENGTH: 35
<212> TYPE: DNA
<213> ORGANISM: Artificial sequence
<220> FEATURE:
<223> OTHER INFORMATION: Synthetic oligonucleotide
```

-continued

```
<400> SEQUENCE: 2
cgtcgtacag atcacacttg gagtatttct ctttc                        35

<210> SEQ ID NO 3
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 3
ccggatcctt atcgtcatcg tcgtacagat c                            31
```

ENHANCING SEROLOGICAL ASSAYS VIA FUSION PROTEINS

CROSS REFERENCE TO RELATED APPLICATION

This application claims the benefit of priority from U.S. Provisional Application No. 62/216,010, filed Sep. 9, 2015, the contents of which are incorporated herein by reference.

FIELD OF THE DISCLOSURE

The present disclosure describes an improved procedure to quantitatively detect immune responses to pathogens (serological tests) using a fusion protein system, such as an anti-cytokine/cytokine fusion protein (ACYF) system.

INCORPORATION BY REFERENCE OF SEQUENCE LISTING

The Sequence Listing in an ASCII text file, named as 32145_SequenceListing.txt of 1 KB, created on Sep. 9, 2016, and submitted to the United States Patent and Trademark Office via EFS-Web, is incorporated herein by reference.

BACKGROUND

Efficient and accurate diagnosis of pathological agents (pathogens) is critical for clinical care, surveillance activities, outbreak control, pathogenesis, academic research, vaccine development, and clinical trials.

A variety of serological assays for identifying immune responses to pathogens have been documented, including, for example, serum neutralization (SN) assay (1), immunofluourescence assay (IFA), complement fixation assay (2), enzyme-linked immunosorbent assay (ELISA), and multiplexing technologies. These assays all follow a common set-up: the antigen/pathogen is used directly in the assay or is coated/coupled on a solid surface/platform to be used for antibody detection. However, these assays usually fail especially if crude or native pathogens are used. Failure can be due to high background and cross-reactivity combined with reduction of specificity and/or sensitivity of the assay, or overall poor analytical sensitivity (lower limit of detection) of the test.

Improvements to the serological assays have been made by using recombinant proteins or synthesized peptide to reduce the background issues. However, these methods have disadvantages as well such as high costs to produce consistent qualities and high quantities of recombinant proteins or antigenic peptides. These assays also use the protein or peptide directly coated/coupled to the solid surface of the assay, which can result in a poor accessibility of certain parts of the proteins.

SUMMARY OF THE DISCLOSURE

This disclosure provides improved serological assays. Specifically, this disclosure provides a method of detecting antibodies against a specific pathogenic antigen, or a group of specific pathogenic antigens, utilizing an antibody-fusion protein system that provides a “bridge” between the solid surface and the pathogenic antigen.

According to this disclosure, an antigen (e.g., an antigen derived from a pathogen) is presented to the serum as a fusion protein between the antigen and a fusion partner, and the fusion protein is anchored to a solid support through an antibody specific for the fusion partner.

The present assays provide multiple advantages over other assays in the art. For example, results obtained from the present assays are highly comparable to results obtained with conventional serological assays such as serum neutralization (SN) testing or ELISA. The present assays can also be multiplexed (several antigens can be measured simultaneously) and are expandable to include more antigens from one pathogens and/or from different pathogens. In contrast, SN test does not allow multiplexing of antigens. Further, the present assays allow for better quantification than SN because the present assays provide continuous data (not titer steps). Moreover, the present assays provide improved signal and dynamic/linear range compared to assays with direct antigen coupling, and provide higher signals on high positive samples and better spread of results than direct antigen assays.

The present assays are associated with a number of unique features that are also advantageous. For example, the present assays do not require purified antigens. Step 1b (FIG. 1B) can be performed with unpurified (crude) solutions containing other proteins, e.g., cell culture supernatants, cell culture lysates or other crude solutions containing the fusion protein. In contrast, conventional assays require purified antigens to couple to a solid support in order to obtain detectable and accurate results. Fusion protein antigens are easier to produce and less expensive than antigens needed for conventional assays. Further, the fusion protein antigens for use in the present assays have an extended storage half-life. For example, supernatants containing the antigens in 5-10% bovine serum albumin can be used for >1 year without loss of signal. Moreover, the fusion protein antigens can be produced in large batches and with convenient procedures (e.g. no-requirements of serum-free solutions for mammalian cell expressed proteins). The present fusion protein system is therefore a low cost method and easy to scale up for large throughput.

BRIEF DESCRIPTION OF THE DRAWINGS

FIGS. 1A-1B: Traditional serological assay setup and an ACYF assay setup. FIG. 1A. Assay set-up and steps for a traditional serological assay, and FIG. 1B. (ACYF) system (right panel) are shown. The steps 1-3 show the sequential order of assay incubation steps for the example of an EHV-1 gC assay. The solid surface can be a bead as shown here, or an ELISA plate or any other solid assay surface.

FIG. 2A-2B: Comparison between EHV-1 serum neutralization (SN) titers and total serum antibodies to EHV-1 glycoproteins gC (FIG. 2A) and gD (FIG. 2B) measured by a EHV-1 Multiplex assay. The analysis was performed using serum samples from 58 horses. Multiplex values are expressed as median fluorescent intensity (MFI). The Spearman rank coefficients for the comparison of SN-titers with gC- or gD-specific total antibody values are both 0.87 (95% CI: 0.79-0.93; $p<0.0001$). The dotted lines show the cut-off between the single SN negative sample (set as SN=1) and samples with low positive SN-titers based on this sample set. Both assay results highly correlate (rsp=0.87, 95% CI: 0.79-0.93, $p<0.0001$). A comparable figure with the same high correlation was obtained for anti-EHV-1 gD antibodies.

FIG. 3: Comparison of ACYF based assay controls with a traditional assay coupling the antigen directly. Three serum samples with known negative (neg), low positive (low) and high positive (high) values were used in adirect assay or an ACYF assay as outlined in FIG. 1A (direct assay) and FIG.

1B (ACYF assay). Blank samples used assay buffer instead of serum in step 2 of the assays (background control). The three sera and the blank were measured with the ACYF assay (four bars on the left) or in the direct assay (four bars on the right, here labeled with DA). The anti-IL-4 bar (fifth bar from the left, shaded) indicates the result after incubating with a different anti-IL-4 antibody again in assay step 3 (this shows the IL-4 gC binding to the beads and provides a maximal signal—note that the 'high' serum sample in the ACYF assay exceeds this 'max' value, while the high serum in the direct assay 'DA high' is lower than the 'max' signal suggesting that some parts of the recombinant gC antigen become inaccessible after direct coupling). The other four bars in the middle labeled with 'no gC' are ACYF assay that are missing the IL-4 gC antigen in step 1b (see FIG. 1B). These four samples indicate that the other assay components including the serum samples do not interact and there is no signal if the antigen is missing in the ACYF assay.

Figure 4A:
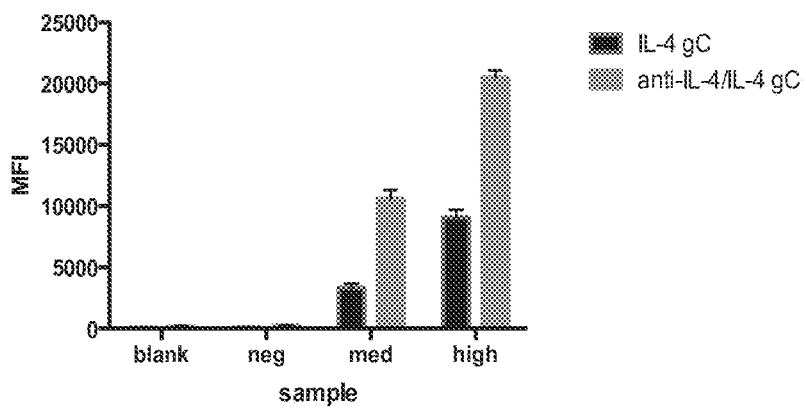
Figure 4B:
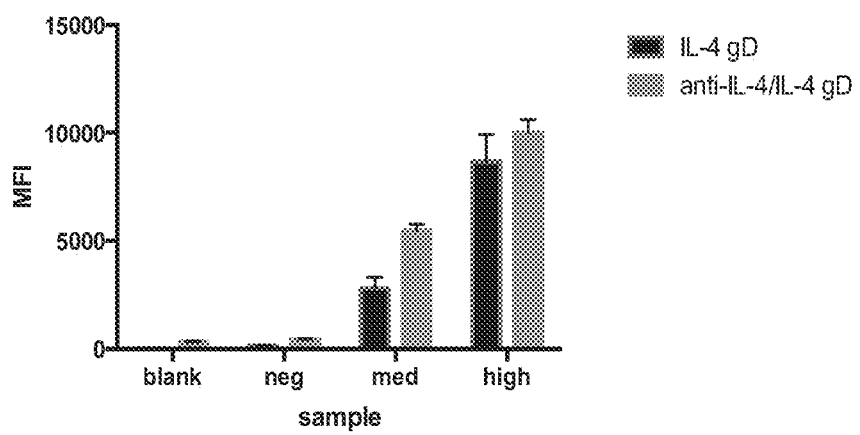

FIGS. 4A-4B: Comparison of multiplex assays using EHV-1 antigens either directly coupled to beads (IL-4 gC or IL-4 gD) or via the anti-IL-4/IL-4 ACYF system. Three serum samples with negative (neg), medium positive (med) or high positive (high) SN-values were used in the assay. In addition a buffer control (blank) was included. The bars show means and standard errors from 20 separate assay runs using the directly coupled gC (FIG. 4A) and gD (FIG. 4B) antigens and 21 separate runs using the anti-IL-4/IL-4 ACYF system. The results show that the MFI signal of the gC assay increased by more than 2-fold for both the medium and the high serum controls by using the anti-IL-4/IL-4 ACYF system (FIG. 4A). For the gD assay a 2-fold increase was also observed for the medium serum and a smaller increase was seen for the high serum (FIG. 4B). This supports the overall increase in the linear quantification range if the same samples are measured in the anti-IL-4/IL-4 ACYF system compared to the fusion protein antigens alone.

Figure 5:
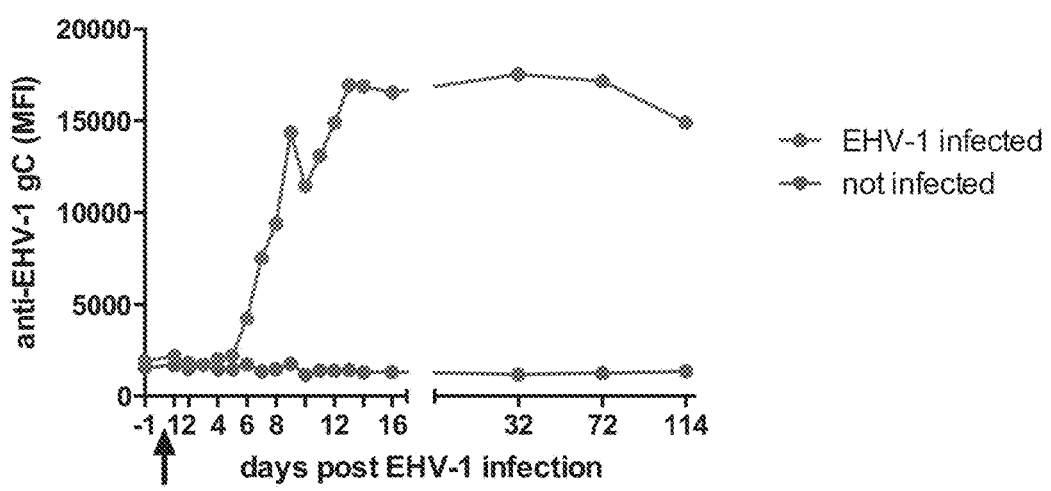

FIG. 5: EHV-1 gC antibodies detected by an ACYF assay after experimental infection of horses with EHV-1. Horses were experimentally infected with EHV-1 (arrow). The control group was not infected with EHV-1. Serum samples of all horses were measured at different times before (day −1) and after infection to determine the anti-gC antibody values. Values are expressed as median fluorescent intensity (MFI).

Figure 6A:
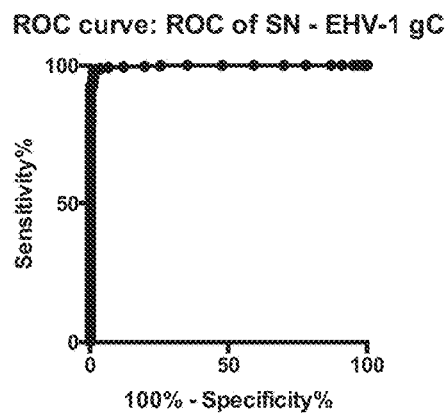
Figure 6B:
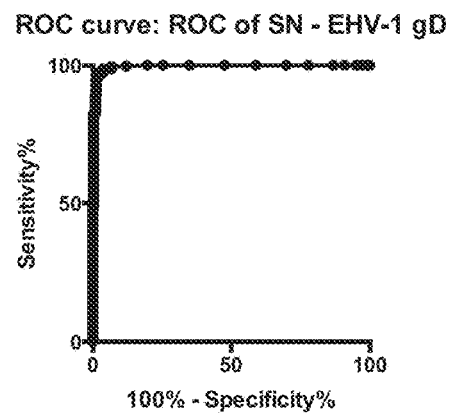

FIGS. 6A-6B: Comparison of EHV-1 Serum Neutralization (SN) and EHV-1 ACYF Multiplex Assay. Parallel sample runs of 509 horse serum samples were done with both SN and ACYF Multiplex assays. The Receiver Operating Characteristic (ROC) curve analysis shows that anti-IL-4/gC and gD Multiplex assay results highly correlate to the gold standard SN testing.

DETAILED DESCRIPTION

Definitions

The term "detecting" is used in the broadest sense to include both qualitative and quantitative measurements of a target molecule, such as an antibody in a biological sample (e.g., a serum sample).

The term "biological sample" includes body samples from an animal, including biogical fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts. In some embodiments, the biological sample is a serum, plasma or urine sample.

The term "animal" includes mammals, for example, human, horse, camel, dog, pig, cow, and sheep. In some embodiments, the animal is an animal suspected to have contracted a disease (e.g., an infection with a pathogen).

The term "antibody" is used in the broadest sense and includes monoclonal antibodies (including agonist, antagonist, and neutralizing antibodies), polyclonal antibodies, multivalent antibodies, multispecific antibodies, and antibody fragments so long as they exhibit the desired binding specificity.

The term "capture reagent" generally refers to a reagent capable of binding and capturing a target molecule in a sample.

The term "plasmids" includes both naturally occurring plasmids in bacteria, and artificially constructed circular DNA fragments.

The term "expression vector" refers to a nucleic acid that includes sequences that effect the expression of a desirable molecule, e.g., a promoter, a coding region and a transcriptional termination sequence. An expression vector can be an integrative vector (i.e., a vector that can integrate into the host genome), or a vector that does not integrate but self-replicates, in which case, the vector includes " " an origin of replication which permits the entire vector to be reproduced once it is within the host cell.

The term "cloning site" refers to a nucleotide sequence, typically present in an expression vector, that includes one or more restriction enzyme recognition sequences useful for cloning a DNA fragment(s) into the expression vector. Where a nucleotide sequence contains multiple restriction enzyme recognition sequences, the nucleotide sequence is also referred to as a "multiple cloning site" or "polylinker".

The term "host cell" refers to a cell into which a nucleic acid, e.g., a nucleic acid heterologous to the host cell, can be introduced by any appropriate means (e.g., transformation, transfection, electroporation, ballistic bombardment, and conjugation) for propagation or expression. A host cell can be eukaryotic or prokaryotic. Representative examples of eukaryotic host cells include mammalian cells, fungal cells, plant cells, and insect cells. Example of fungal host cells is yeast, e.g., strains of *Saccharomyces cerevisiae*. Representative examples include bacteria such as, for example, *Escherichia coli*.

Fusion Protein

The present assays utilize a fusion protein between a target antigen and a fusion partner.

Generally speaking, the fusion partner can be any protein as long as the serum sample being tested does not contain antibodies for such protein. In some embodiments, the fusion partner is a self protein (i.e., a protein naturally present in the same animal species as the animal subject whose serum is being tested), a cytokine such as IL-2, IL-4, IL-5, IL-10, IL-13 or IL-31. In a specific embodiment, the fusion partner is IL-4.

In some embodiments, the antigen in the fusion protein is an antigen from a pathogen. In some embodiments, the pathogen is a virus, a bacterium or a fungus which can cause illnesses. In one embodiment, the antigen is a cell surface molecule of a pathogen, or antigenic parts or fragments thereof. Examples of pathogenic cell surface molecules include, but are not limited to, viral envelope glycoproteins, and bacterial or yeast cell wall molecules such as peptidoglycans and teichoic acids. In other embodiments, the antigen is a soluble protein (i.e., not associated with or attached to the cell surface). In a specific embodiment, the antigen is an envelope glycoprotein of Equine Herpesvirus EHV-1 gC or EHV-1-gD, or an antigenic fragment thereof. By "antigenic fragment" it is meant to include a fragment of a molecule that is of sufficient size to provoke an immune response (e.g., an antibody response), typically a size of at least 6, 7, 8 or 9 amino acids.

In a specific embodiment, the antigen is an envelope protein of Human Immunodeficiency Virus (HIV), or an antigenic fragment thereof.

A fusion protein can be made by creating a nucleic acid molecule encoding the fusion protein and expressing the fusion protein from such nucleic acid in a recombinant expression system. The nucleic acid molecule encoding the fusion can be generated by linking the nucleic acid sequence encoding the fusion partner in frame with the nucleic acid sequence encoding the antigen. Methods for constructing a fusion protein are known in the art (see Sambrook J. et al., Molecular Cloning, Cold Spring Harbor Press, New York (2001)).

In one embodiment, the fusion partner is fused to the N-terminus of the antigen. In this orientation, the fusion partner can be used as an N-terminal tag for detection and purification of the fusion protein. In addition, when the full length coding sequence for the fusion partner is used, the leader sequence (secretory signal peptide), if any, of the fusion partner (e.g., cytokine) can facilitate the secretion of the fusion protein. Alternatively, other appropriate leader sequences, suitable for guiding the fusion protein to the ER and the secretory pathway in the host cell, can be used instead of the leader sequence of the fusion partner and linked to the mature sequence of the cytokine.

In another embodiment, the fusion partner is fused to the C-terminus of the antigen. In making a fusion of this orientation, preferably the mature form of the fusion partner, rather than the full-length sequence including the leader sequence, is used. The fusion protein can rely on the leader sequence of the antigen if present, or a heterologous leader sequence (from a protein other than the antigen) functional in the host cell, to achieve secretion of the fusion protein.

In still another embodiment, a spacer can be incorporated between the fusion partner and the antigen. By "spacer" is meant a short peptide sequence that joins the fusion partner and the antigen, yet preserves some distance between the two proteins such that both the cytokine and antigen can properly fold independently. Generally, the spacer consists of between 2 or 3 amino acids to 50 amino acids, typically between 3 to 25, or 3 to 20, or 3 to 15 amino acids. In a specific embodiment, the space consists of 3-10 amino acids. Although there is no specific restriction on the selection of amino acids for the spacer region, the amino acids can be selected to accommodate the folding, net charge, hydrophobicity or other properties of the fusion protein. Typical amino acids for use in a spacer region include Gly, Ala, Ser, Thr and Asp.

One of skill would recognize that modifications can be made to a fusion partner (e.g., a cytokine), an antigen or the fusion protein without diminishing their biological activities. Some modifications may be made to facilitate the cloning, expression, or incorporation of the constituent molecules into a fusion protein. For example, amino acids can be placed on either terminus to create conveniently located restriction sites or termination codons; and a methionine can be added at the amino terminus to provide an initiation site.

Recombinant Expression of the Fusion Protein

For recombinant expression of a fusion protein, a nucleic acid molecule encoding the fusion protein is generally placed in an expression vector in an operable linkage to a promoter (such as the T7, trp, or lambda promoters for expression in bacteria, or a CMV promoter for expression in mammalian cells) and a 3' transcription termination sequence, and optionally additional suitable transcriptional and/or translational regulatory elements such as a transcription enhancer sequence and a sequence encoding suitable mRNA ribosomal binding sites. Additional sequences that can be included in the expression vector include an origin of replication, and a selection marker gene to facilitate identification of transformants such as genes conferring resistance to antibiotics (e.g., the amp, kana, gpt, neo, and hyg genes).

Host cells suitable for use in the recombinant expression of the fusion protein include bacterial cells such as E. coli, and eukaryotic cells including but not limited to yeast, insect cells (e.g. SF9 cells), and mammalian cells such COS, CHO and HeLa cells.

The expression vectors can be introduced into a host cell by well-known methods such as calcium chloride transformation for bacterial cells, and calcium phosphate treatment or electroporation for mammalian cells. Cells transformed by the expression vectors can be selected based on the phenotype provided by the selectable marker gene.

Even though the present assay system does not require purification of the fusion proteins to work, once expressed, the recombinant fusion proteins can be purified according to standard methods available in the art, such as ammonium sulfate precipitation, affinity columns, chromatography, gel electrophoresis, among others. In one embodiment, the fusion protein is purified based on affinity chromatography using antibodies specific for the cytokine component in the fusion protein. In another embodiment, the fusion protein is separated by immunoprecipitation with the anti-cytokine antibody and that immunoprecipitate is used for the next steps of the assay.

Capture Reagent and Assay

To perform the present assays for detecting immune responses to an antigenic entity (e.g., a pathogen), a capture reagent is formed first, which is composed of a fusion protein between an antigen from the antigenic entity and a fusion partner (e.g., IL-4), bound to an antibody directed against the fusion partner (e.g., a monoclonal antibody against IL-4), which is in turn conjugated (i.e., bound) to a solid surface (e.g., beads or an ELISA plate).

In some embodiments, the antibodies are conjugated to a solid surface such as beads (e.g., fluorescent beads). In other embodiments, the solid surface is an ELISA plate or any other solid assay surface.

The capture reagent is then brought in contact with a serum sample and incubated to allow binding of any antibodies in the serum that are specific to the antigen in the fusion protein, to the antigen. After washing, any bound antibody against the antigen can be detected by anti-Ig antibodies.

In some embodiments, the presence of different antibodies directed towards different antigens (from the same or different pathogens) can be detected simultaneously in a multiplexed manner. For example, to detect two different antigens, a capture reagent containing a first and second reagents is provided, wherein the first reagent comprises a first fusion protein between a first antigen and a fusion partner (e.g., IL-4), bound to an antibody directed against the fusion partner (e.g., a monoclonal antibody against IL-4), which antibody is bound to a first solid substrate (e.g., beads of a first fluorescent color), and the second reagent is also provided that comprises a second fusion protein between a second antigen and the same fusion partner (e.g., IL-4), bound to the antibody directed against the fusion partner, which antibody is immobilized to a second solid substrate (e.g., beads of a second fluorescent color); the capture reagent is brought into contact with a serum sample to allow binding of any antibodies in the serum that are specific to the first antigen or the second antigen to bind; and after washing, any bound antibody against the antigen can be detected by secondary antibodies (e.g., anti-Ig antibodies).

In other embodiments, the presence of multiple (i.e., two or more) different antibodies directed towards multiple different antigens (from the same or different pathogens) are detected simultaneously in a multiplexed manner wherein the same solid substrate (e.g., an identical, single solid substrate such as an ELISA plate) is used for a capture reagent containing a mixture of multiple fusion protein based reagents. In one specific embodiment, the solid substrate is an ELISA plate or another suitable protein-binding assay plate. In this instance, to detect multiple antibodies such as two antibodies, a capture reagent containing a mixture of a first and second reagents is provided, wherein the first reagent comprises a first fusion protein between a first antigen and a fusion partner (e.g., IL-4), bound to an antibody directed against the fusion partner (e.g., a monoclonal antibody against IL-4), which antibody is bound to the solid substrate (e.g., an ELISA plate), and the second reagent is also provided that comprises a second fusion protein between a second antigen and the same fusion partner (e.g., IL-4), bound to the antibody directed against the fusion partner, which antibody is immobilized to the same solid substrate; the capture reagent is brought into contact with a serum sample to allow binding of any anybody in the serum that is specific to the first antigen or the second antigen; and after washing, any bound antibody against the antigen can be detected by secondary antibodies (e.g., anti-Ig antibodies).

In yet other embodiments, the presence of multiple (i.e., two or more) different antibodies directed towards multiple different antigens (from the same or different pathogens) are detected simultaneously in a multiplexed manner wherein a different solid substrate is used for each individual fusion protein based reagent conjugated with a different antigen. In one specific embodiment, the solid substrate is a bead or another suitable protein-binding entity or substrate. In this instance, to detect multiple antibodies such as two antibodies, a capture reagent containing a mixture of a first and second reagents is provided, wherein the first reagent comprises a first fusion protein between a first antigen and a fusion partner (e.g., IL-4), bound to an antibody directed against the fusion partner (e.g., a monoclonal antibody against IL-4), which antibody is bound to a first solid substrate (e.g., a first group of beads); and the second reagent is also provided that comprises a second fusion protein between a second antigen and the same fusion partner (e.g., IL-4), bound to the antibody directed against the fusion partner, which antibody is immobilized to a second solid substrate (e.g., a second group of beads). The first and second groups of beads can be made of the same materials (e.g., fluorescent beads), and can differ in color for example (e.g., fluorescent beads in the same or different colors), for convenient handling and distinction. The first and second reagents can be mixed together to form the capture reagent which is then brought into contact with a serum sample to allow binding of any anybody in the serum that is specific to the first antigen or the second antigen; and after washing, any bound antibody against the antigen can be detected by secondary antibodies (e.g., anti-Ig antibodies).

In one embodiment, the ACYF system is used for antibody isotype analysis. In this embodiment, an ACYF assay (e.g., an IL-4 based assay) employs a detection antibody specific for antibodies of particular isotype. For example, instead of using a polyclonal anti-horse IgG (H+L) antibody which detects heavy and light chains of horse IgG antibodies, isotype-specific detection reagents are used (e.g., anti-IgG1, anti-IgG2, anti-IgG3, anti-IgG4 anti-IgM, anti-IgE, or anti-IgA etc.). In contrast, a Serum Neutralization (SN) is not suitable for isotype analysis.

Examples of common conventional immunoassays are direct assays and sandwich assays. In direct assays, one primary antibody attaches directly to an antigen immobilized on a surface such as an ELISA plate, fluorescent bead, or a membrane. In sandwich assays, two antibodies (a capture antibody and a detection antibody) are used to capture and detect an antigen. Direct assays can be used to detect antibodies in a sample, whereas sandwich assays are suitable for detecting antigens.

The ACYF assays, described herein, are surprisingly superior over conventional serological assays.

Firstly, ACYF assays can utilize unpurified solutions containing the fusion proteins/antigens to prepare the capture reagent comprising a fusion protein coupled to an antibody specific for the fusion partner in the fusion protein, immobilized to a solid substrate. "Unpurified solutions" or "crude solutions" as used herein refer to solutions that have not been purified with a protein purification method such differential solubilization, affinity chromatography, ion exchange chromatography, hydrophobic interaction chromatography, free-flow electrophoresis, size exclusion chromatography, filtration or dialysis. Examples of unpurified (crude) solutions include, but are not limited to, cell culture supernatants, cell culture lysates or extracts, or other crude biological fluids containing a fusion protein. In contrast, direct assays require purified proteins/antigens to coat the solid substrate, and sandwich assays require specific antibodies to recognize the antigen before immobilizing to the solid substrate. Using crude/non-purified antigen sources increase the background noise and decrease the specificity of direct assays. Sandwich assays fail when there is no antibody available against the antigen, or when the available antibody is of low quality (low affinity and/or specificity). On the other hand, ACYF assays use antibodies against the known fusion partner, regardless of what the antigen is. An additional advantage of such a setup is that the antibody against the known fusion partner can be selected to have high specificity and selectivity, thereby reducing any non-specific interactions. Therefore, ACYF assays, with components that are easier and cheaper to produce than other conventional assays, produce surprisingly superior results even when used with crude/non-purified antigens.

Figure 3:
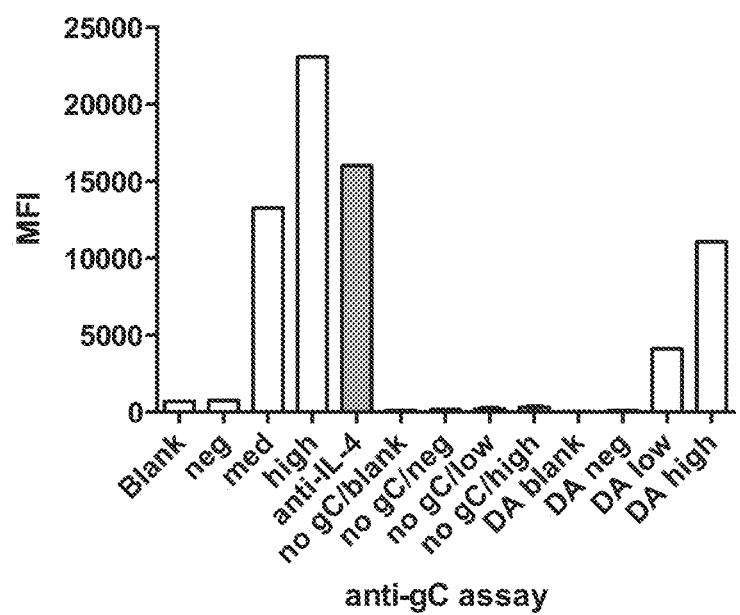

Secondly, ACYF assays produce signals that can be measured as continuous data over a wider dynamic/linear range than the conventional assays. By "continuous data" it is meant data without breaks in a selected range, as opposed to discrete data. Conventional assays such as a Serum Neutralization assay typically measure samples prepared with two fold dilutions, wherein each subsequent sample produces a discrete signal that differs by two folds from next dilution step. On the other hand, ACYF assays disclosed herein produce signals which have an infinite number of possible measurable values, hence providing "continuous data". In some embodiments, the signal produced from an ACYF assay exceed the maximum (saturated) signal from a direct assay positive control, and in specific embodiments, is at least 25%, 50%, 75%, 100%, 150%, 200%, 250%, 300%, 400%, 500% greater than the signal from the same sample measured by a conventional assay. For example, see FIG. 3 comparing the fourth (ACYF-high sample), fifth (direct assay, positive control) and thirteenth (direct assay—high sample) bars. Also see FIG. 4A and FIG. 4B, which show that ACYF assay gives a more enhanced signal than a conventional direct assay setup using the same samples.

In some embodiments, an ACYF assay can provide continuous signal readouts (data) ranging from about 50 MFI (median fluorescent intensity) to about 20,000 MFI, which enables the assay to separate and spread the data over a wide dynamic/linear quantification range where all values in the range are possible. On the other hand, the Serum Neutralization (SN) assay has a dynamic range between about 4 MFI and about 4096 MFI. In addition, due to the two-fold tittering/dilution steps involved in SN, samples with similar target antibody concentrations may produce the same discrete MFI value, even though the samples are not identical. Therefore, an ACYF system allows for superior separation between samples.

Thirdly, fusion proteins used in ACYF assays can be stored for extended periods of time. For example, supernatants comprising the antigens (the fusion proteins) and 5-10% bovine serum albumin (BSA) can be used in an ACYF assay without loss of signal strength even after more than 1 year in storage. ACYF fusion proteins can be stored at 4° C., −20° C., −80° C. or in liquid nitrogen.

Kits

In further embodiments, this disclosure provides a kit for detecting immune responses in a mammal biological sample. The kit can include an expression vector, wherein said vector comprises from 5' to 3', a promoter, a fusion partner coding sequence, a cloning site located at or near the C-terminus of the fusion partner coding sequence for insertion of a nucleic acid coding for an antigen of interest to form a fusion with said fusion partner, and a 3' transcription termination sequence; a host cell for recombinant expression of the fusion protein; an antibody against the fusion partner; and a solid substrate, instructions, and reagents for detecting the presence of antibodies to the antigen of interest.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

Example 1: Comparing Multiplex ACYF System with Serum Neuralization (SN) for the Detection of Equine Herpesvirus Type 1 (EHV-1) in Serum Samples Of all viral infections in horses, Equine herpesvirus 1 (EHV-1) is among the most costly because of the abortions, neonatal mortality, respiratory and neurological diseases it causes in horses. Infected animals develop antibodies against several antigens of the virus including the envelop glycoproteins gC and gD. Detecting these antibodies can reflect disease stage and help determine the course of treatment and quarantine of the sick animal.

Conventional Serum Neutralization (SN) test is the gold standard for measuring anti-EHV antibody titers in serum samples from infected horses. However, SN tests are very time-consuming and cumbersome to perform. In this example, the assay of this invention (the ACYF system) was compared to a conventional SN test. This was done using the example of an IL-4 ACYF system in a bead-based multiplex assay for the detection of antibodies to equine herpesvirus type 1 (EHV-1) in serum samples (FIG. 1A). The assay can easily be used for more antigens (e.g., two to four antigens) and is further expandable to other pathogens and antigens. This example uses just two antigens to keep the essential data simple.

Materials and Methods

Serum Neutralization (SN) Test

Serum Neutralization was performed as described in Wagner et al. (2015) (1). In brief, two-fold serial dilutions of heat inactivated serum samples or controls were incubated with a constant concentration of virus. After 1.5 h of incubation, RK13 cells were added in suspension. The 50% neutralizing dilution was determined after 3 days based on the presence or absence of cytopathic effects in the wells.

IL-4 Expression Vector

As described in Wagner et al. (2012) (3), an expression vector containing equine IL-4 (411 bp) and a sequence encoding an enterokinase digestion site (EK; 24 bp) was generated using the mammalian expression vector pcDNA3.1 (−)/Myc-His, version B (Invitrogen, Carlsbad, Calif., USA). The IL-4 expression vector allowed cloning of the gene of interest into the multiple cloning site (MCS) downstream of the IL-4/EK sequence for expression of rIL-4 fusion proteins (FIG. 1A). The complete equine IL-4 gene (Genbank Accession GU139701) without stop codon was amplified in two steps with (1) primers containing a NotI restriction site (forward—5'-gcggccgcatgggtctcacctac-caactg-3') (SEQ ID NO: 1) and the partial EK sequence (reverse—5'-cgtcgtacagatcacacttggagtatttctctttc-3') (SEQ ID NO: 2) and (2) the same forward primer together with a primer for the complete EK sequence with a BamHI restriction site (reverse 2—5'-ccggatccttatcgtcatcgtcgtacagatc-3') (SEQ ID NO: 3).

Transfection and Fusion Protein Production

Transfection of Chinese Hamster Ovary (CHO) cells and generation of a stable EHV-1 gC/IL-4 and EHV-1 gD/IL-4 transfectant were performed as previously described for other fusion proteins in Wagner et al. 2005 (4). Cell supernatants containing the fusion proteins were prepared as described in Wagner et al. 2005 (4).

Fluorescent beads of different color codes are coupled with the equine anti-IL-4 mAb (e.g. clone13G7) according to protocols previously described (Wagner et al 2015 (1)).

One coupled anti-IL-4 bead batch (one color code) was then incubated with cell culture supernatant containing EHV-1 gC/IL-4 and the other anti-IL-4 bead batch (second color code) was incubated with supernatant containing EHV-1 gD/IL-4. The incubation was performed in a sterile tube, keeping each bead separate, on the rocker platform wrapped in aluminum foil for 30 minutes. Afterwards, the beads were washed three times with assay buffer (PBN) to remove the supernatant and any unbound EHV-1 proteins. Beads can be used right afterwards or stored in this format for several months.

ACYF Assay

For the ACYF assay, beads were resuspended in PBN and the required amounts for the assay and both the EHV-1 gC/IL-4 and EHV-1 gD/IL-4 beads were mixed together at this step. A PBN blank (negative control), standardized serum controls (positive controls) and individual patient samples were added to the plate. Serum samples were diluted 1:400 in PBN and 50 μl per well was added. Subsequently, the EHV-1 gC/IL-4-gD/IL-4 mixture was added to the plate at 50 μl per well. The plate was wrapped at this point to avoid bleaching by light. Samples and beads were incubated for 30 minutes on a shaker at room temperature. The plate was washed afterwards and a biotinylated goat anti-horse polyclonal or monoclonal antibody was added for detection (50 μ/well). Incubation was again for 30 minutes on a shaker. The plate was washed again and a solution of streptavidin-phycoerythrin (50 μl/well) was added for another 30 minutes. After a last wash the plate was filled with 100 μl PBN and beads are resuspended for 15 minutes on a shaker. Then, the plate was read in the multiplex analyzer.

Receiver Operating Characteristic (ROC) curve analysis was done as described in Hanley (1998) (5) and Hajian-Tilaki (2013) (6). The ROC curve was used to compare a new assay (e.g., Anti-IL-4/IL-4-gC, in this case) to a known assay (e.g., the gold standard SN assay, in this case). If the assays produce results that match perfectly, the ROC curve would go steeply up the Y-axis and then in a 90 degree angle along the horizontal upper line. On the other hand, a meaningless assay (50% false results, random overlap in results) would produce a diagonal line (45 degree) from the lower left corner to the upper right corner of the ROC plot.

Results

Figures 2A, 2B:
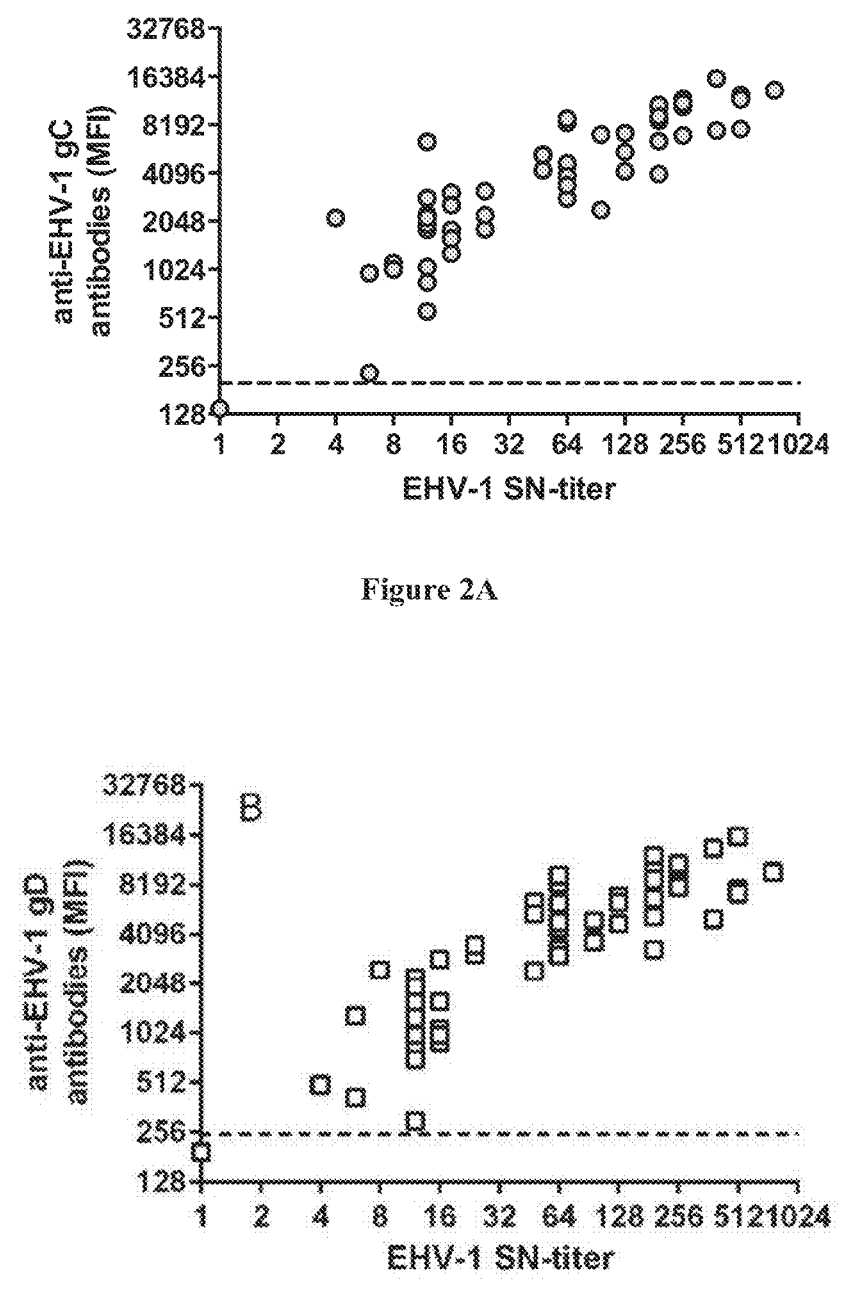

The EHV-1 Multiplex assay correlated highly with EHV SN-titers (FIGS. 2A-2B). SN-testing is the currently accepted gold standard for EHV antibody testing. This shows that the ACYF assay is a valid test to use for EHV-1 detection and provides an advanced alternative to SN testing because the ACYF assay results in continuous data, and has a wider dynamic range which overall improves antibody quantification.

An ACYF based assay, in which the antigen was coupled via an anti-cytokine antibody showed minor background and generated signals that were (i) specific to the targeted antigen and (ii) higher than the values of a traditional serological assay, in which the antigen was coupled directly to the assay surface. This is demonstrated in an exemplary EHV-1 gC ACYF assay in FIG. 3.

Next, a traditional serological assay was compared to the ACYF based assay using more than one antigen and several repeated runs, as demonstrated using two EHV-1 antigens, IL-4 gC and IL-4 gD in FIGS. 4A-4B. A direct comparison of the same serum samples in a traditional assay versus a ACYF system showed that a better distribution of assay results (wider spread of results) and higher signals were achieved when the samples were measured using the ACYF system.

An ACYF EHV-1 assay was also shown to be useful for tracking EH-1 infection in infected horses EHV-1 (FIG. 5).

A ROC curve analysis of 509 horse serum samples run in parallel shows that the results from an anti-IL-4/gC and gD multiplex assay highly correlate with the gold standard SN testing (FIG. 6A and FIG. 6B).

REFERENCES (1) B. Wagner et al., Antibody and cellular immune responses of naïve mares to repeatedvaccination with an inactivated equine herpesvirus vaccine, *Vaccine* 33 (2015); 5588-5597

(2) Kydd J H, Townsend H G G, Hannant D. The equine immune response toequine herpesvirus-1: the virus and its vaccines. *Vet Immunol Immunopathol* (2006); 111: 15-30.

(3) Wagner B, Hillegas J, Babasyan S. 2012. Monoclonal antibodies to equine CD23 identify the low-affinity receptor for IgE on subpopulations of $IgM^+$ and $IgG1^+$ B-cells in horses. *Vet. Immunol. Immunopathol.,* 146: 125-134.

(4) Wagner, B., Robeson, J., McCracken, M., Wattrang, E., Antczak, D. F., 2005. Horse cytokine/IgG1 fusion proteins—mammalian expression of biologically active cytokines and a system to verify antibody specificity to equine cytokines. *Vet. Immunol. Immunopathol.* 105, 1-14.

(5) Hanley, James A. “Receiver operating characteristic (ROC) curves.” *Encyclopedia of Biostatistics* (1998)

(6) Hajian-Tilaki, Karimollah. “Receiver operating characteristic (ROC) curve analysis for medical diagnostic test evaluation.” *Caspian Journal of Internal Medicine* 4.2 (2013): 627.

What is claimed is:

1. A method for detecting antibodies in a biological sample, comprising:

(a) providing a capture reagent comprising a first reagent comprising a first fusion protein between a first antigen and a fusion partner, an antibody specific for the fusion partner, and a first solid substrate, wherein the fusion partner is a cytokine, and wherein the first fusion protein is bound to the antibody and the antibody is immobilized to the first solid substrate;

(b) incubating a biological sample with the capture reagent to allow for antibodies present in the sample to bind to the first antigen in the capture reagent; and (c) detecting antibodies bound to the first antigen.

2. The method of claim 1, wherein the capture reagent further comprises a second reagent comprising a second fusion protein between a second antigen and the fusion partner, the antibody specific for the fusion partner, and a second solid substrate, wherein the second fusion protein is bound to the antibody and the antibody is immobilized to the second solid substrate, wherein the second antigen is different from the first antigen.

3. The method of claim 2, wherein the first fusion protein is a fusion of EHV-1 gC and IL-4, and the second fusion protein is a fusion between EHV-1 gD and IL-4.

4. The method of claim 2, wherein the first solid support is fluorescent beads of a first color, and the second solid support is fluorescent beads of a second color, wherein the first and second colors are the same or different.

5. The method of claim 2, wherein the first solid substrate and the second solid substrate are the same.

6. The method of claim 5, wherein the solid substrate is an ELISA plate.

7. The method of claim 1, wherein the fusion protein is provided in an unpurified form.

8. The method of claim 7, wherein the fusion protein is provided by lysate of a host cell that expresses the fusion protein.

9. The method of claim 1, wherein the biological sample is blood, plasma, serum, saliva, urine, synovial and cerebrospinal fluid, milk or tissue homogenates.

10. The method of claim 1, wherein the biological sample is obtained from an animal.

11. The method of claim 10, wherein said animal is a mammal.

12. The method of claim 10, wherein said mammal is selected from the group consisting of human, horse, dog, camel, pig, cow, and sheep.

13. The method of claim 11, wherein the fusion partner is selected from the group consisting of IL2, IL-4, IL-5, IL-10, IL-13 and IL-31.

14. The method of claim 13, wherein said fusion partner is IL-4.

15. The method of claim 1, wherein said antigen is a cell surface molecule of a pathogen or an antigenic fragment thereof.

16. The method of claim 15, wherein the pathogen is selected from a virus, a bacterium, or a fungus.

17. The method of claim 1, wherein said antigen is a soluble protein of a pathogen or an antigenic fragment thereof.

18. The method of claim 17, wherein the pathogen is selected from a virus, a bacterium, or a fungus.

19. The method of claim 1, wherein said antigen is EHV-1 gD or an antigenic fragment thereof, or EHV-1 gC of an antigenic fragment thereof.

20. The method of claim 1, wherein said fusion partner is fused to the N-terminus of said antigen.

21. The method of claim 1, wherein said fusion partner is fused to the C-terminus of said antigen.

22. The method of claim 1, wherein the first solid substrate is beads.

23. The method of claim 1, wherein antibodies are detected in step (c) by using isotype-specific antibodies.

24. A kit for detecting immune responses in a mammal biological sample, comprising an expression vector, wherein said vector comprises from 5' to 3', a promoter, a cytokine coding sequence, a cloning site located at or near the C-terminus of the cytokine coding sequence for insertion of a nucleic acid coding for an antigen of interest to form a fusion with said cytokine, and a 3' transcription termination sequence;

a host cell for recombinant expression of said fusion protein;

an antibody against said cytokine;

a solid substrate, instructions, and reagents for detecting the presence of antibodies to the antigen of interest.

* * * * *